(12) United States Patent
Slusher et al.

(10) Patent No.: US 12,023,177 B2
(45) Date of Patent: Jul. 2, 2024

(54) BODY IMAGING DEVICES, SYSTEMS, AND METHODS

(71) Applicants: Gianna Slusher, Westfield, NJ (US); Caitlin Reina, Douglaston, NY (US)

(72) Inventors: Gianna Slusher, Westfield, NJ (US); Caitlin Reina, Douglaston, NY (US)

( * ) Notice: Subject to any disclaimer, the term of this patent is extended or adjusted under 35 U.S.C. 154(b) by 992 days.

(21) Appl. No.: 16/935,912

(22) Filed: Jul. 22, 2020

(65) Prior Publication Data

US 2021/0030361 A1    Feb. 4, 2021

Related U.S. Application Data

(60) Provisional application No. 62/880,931, filed on Jul. 31, 2019.

(51) Int. Cl.
*A61B 5/00* (2006.01)

(52) U.S. Cl.
CPC .......... *A61B 5/6835* (2013.01); *A61B 5/0064* (2013.01); *A61B 5/0077* (2013.01); *A61B 5/0091* (2013.01)

(58) Field of Classification Search
CPC ..... A61B 5/6835; A61B 5/015; A61B 5/0091; A61B 5/0077; A61B 5/0064
See application file for complete search history.

(56) References Cited

U.S. PATENT DOCUMENTS

| | | | |
|---|---|---|---|
| 6,333,826 B1 | 12/2001 | Charles | |
| 2007/0213617 A1* | 9/2007 | Berman | A61B 5/0091 600/473 |
| 2010/0312136 A1 | 12/2010 | Cozzie | |
| 2012/0150034 A1 | 6/2012 | DeFreitas et al. | |
| 2015/0018691 A1 | 1/2015 | Stepien et al. | |
| 2019/0166312 A1 | 5/2019 | Tashayyod et al. | |
| 2019/0209106 A1 | 7/2019 | Bechtold et al. | |

FOREIGN PATENT DOCUMENTS

CN    106572798 A  *  4/2017  .........  A61B 10/0041

OTHER PUBLICATIONS

International Search Report issued in corresponding PCT Application No. PCT/US2020/043276, prepared by Office Blane R. Copenheaver, mailed on Oct. 15, 2020.

* cited by examiner

*Primary Examiner* — Mark R Gaworecki
(74) *Attorney, Agent, or Firm* — Locke Lord LLP; Gabrielle L. Gelozin

(57) ABSTRACT

A system for imaging a portion of a body can include a mount configured to hold an imaging device carrier. The mount can include a plurality of discreet positions configured to hold the imaging device carrier, for example.

15 Claims, 6 Drawing Sheets

BODY IMAGING DEVICES, SYSTEMS, AND METHODS

CROSS-REFERENCE TO RELATED APPLICATIONS

This application claims priority to and the benefit of U.S. Provisional Application No. 62/880,931, filed Jul. 31, 2019, the entire contents of which are herein incorporated by reference in their entirety.

FIELD

This disclosure relates to body imaging devices, systems, and methods, e.g., for breast cancer screening.

BACKGROUND

Breast cancer is very prevalent in women, and it is estimated that one in eight women will get breast cancer. Early detection is key for survival in women in order to reduce the mortality rate. Mammography is currently the gold standard for diagnosing breast cancer. Although mammograms are effective, they are usually not recommended by physicians until a woman is forty-five years old. This leaves out approximately twenty-seven thousand American women each year who will get breast cancer under the age of forty-five. Women who are forty-five years old and older are usually only recommended to get mammograms once per year, which is relatively infrequent. Mammograms are typically not distributed more than once per year due to the fact that they expose the patient to harmful radiation, which in turn can cause more breast cancer. Mammograms are also painful and invasive, which causes many women to try and avoid them. Mammograms must be performed by physicians, due to the fact that they involve x-ray technology. Many women, particularly in east Asian countries, feel embarrassed to go to the doctor for mammograms as they involve the woman to expose herself, and these women therefore avoid breast examination.

Self-breast exams are convenient and can be done at home; however, they are no longer recommended by the American Cancer Society due to the number of false positives that are produced. This is mainly due to the fact that they are often complicated for the women to conduct them properly, and many women will mistakenly perceive benign growths and cysts as cancerous tumors. This causes the woman to undergo unnecessary screening which in time could lead to more harm to the woman, both emotionally and physically.

Thermography is a non-invasive screening method for breast cancer detection. Thermal imaging captures infrared emissions from the human body, mapping the surface temperature on the skin. Cancerous breast tumors can typically change the surface temperature of the breast by one to four degrees centigrade warmer than healthy breast tissue. This is due to the fact that cancerous breast tumors require an excess blood flow, which increases the temperature of the tumor and the veins around it. Thermography can also be used to analyze vascular patterns, which describes the characteristics of blood flow throughout the body, specifically analyzing blood flow in the breasts.

A significant benefit of thermography is the fact that thermal imaging does not detect benign growths and cysts, due to the fact that they do not require excess blood flow, and therefore do not heat up. This prevents a large number of false positive results, and therefore prevents a woman from undergoing unnecessary harmful screening. Also, thermography is unaffected by breast density, hormonal changes, and breast implants. This is specifically helpful for younger women as they typically have dense breasts that are difficult to screen with mammography.

Existing thermography systems have been only available in doctor's office in place of mammogram, or in a contact thermography system for at home use which required sending away the results to be analyzed. Contact thermography cannot provide consistent images because the device is handheld and the position of the device is variable each time. Accordingly, existing systems cannot provide consistent, convenient, inexpensive, and safe breast thermography, e.g., for early screening and detection.

Such conventional methods and systems have generally been considered satisfactory for their intended purpose. However, there is still a need in the art for improved body imaging devices, systems, and methods. The present disclosure provides a solution for this need.

SUMMARY

A system for imaging a portion of a body can include a mount configured to hold an imaging device carrier. The mount can include a plurality of discreet positions configured to hold the imaging device carrier, for example.

The mount can include a holder portion configured to at least partially surround a portion of a human body and/or to provide a plurality of imaging angles of a human body. In certain embodiments, the holder portion can have an arcuate shape. The arcuate shape can be a half ellipse. Any other suitable shape is contemplated herein.

The holder portion can include a plurality of notches defined therein configured to receive the imaging device carrier. The plurality of notches can include three or more notches, e.g., five notches, each notch equally spaced apart from each other along the holder portion. Any other suitable number of notches and/or spacing (e.g., unequal spacing) are contemplated herein.

The mount can include a wall mount portion configured attach to a wall bracket or portion thereof, and/or to mount directly to a wall. The wall mount portion can be straight and/or flat.

The system can include a first portion of a wall bracket configured to be attached to the wall mount portion of the mount and a second portion of a wall bracket configured to attach to a wall such that the mount can be configured to removably and/or moveably connect to the wall to position the mount in the same position during imaging. In certain embodiments, the wall bracket can be a z clip.

In certain embodiments, the system can include the imaging device carrier. The imaging device carrier can be configured to be removably and/or moveably held by the mount. The imaging device carrier and/or the mount can include a level disposed thereon to ensure that the imaging device carrier is level at each use. The imaging device carrier can be configured to hang from the mount. The imaging device carrier can include a clamp configured to hold an imaging device.

In certain embodiments, the system can include an imaging module configured to receive one or more thermal images of the body portion from the imaging device and to allow a user to screen for a medical condition of the body portion. In certain embodiments, the body portion can be breasts, and the medical condition can be breast cancer. The imaging module can be configured to present one or more thermal images of the body portion to a display for a user to review, and/or to allow the user to monitor changes of a plurality of thermal images of the body portion over time, and/or to analyze the one or more thermal images for a medical condition. The imaging module can include any other suitable module(s) having any other suitable function (s). The imaging module can be configured to perform any suitable method(s) and/or function(s) disclosed herein.

In accordance with at least one aspect of this disclosure, a mount for imaging a body part can be configured to hold an imaging device carrier and can include a plurality of discreet positions configured to hold the imaging device carrier. Any suitable embodiment of a mount disclosed herein, e.g., as described above, is contemplated herein.

In accordance with at least one aspect of this disclosure, a non-transitory computer readable medium can include computer executable instructions configured to cause a computer to perform a method. The method can include receiving one or more thermal images of a body portion from an imaging device, analyzing the one or more thermal images for a medical condition of the body portion, and presenting the one or more thermal images and/or analysis and/or one or more derivative images based on the one or more thermal images to a user for evaluating and/or monitoring the body portion. Any other suitable method(s) and/or portion(s) thereof are contemplated herein.

These and other features of the embodiments of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
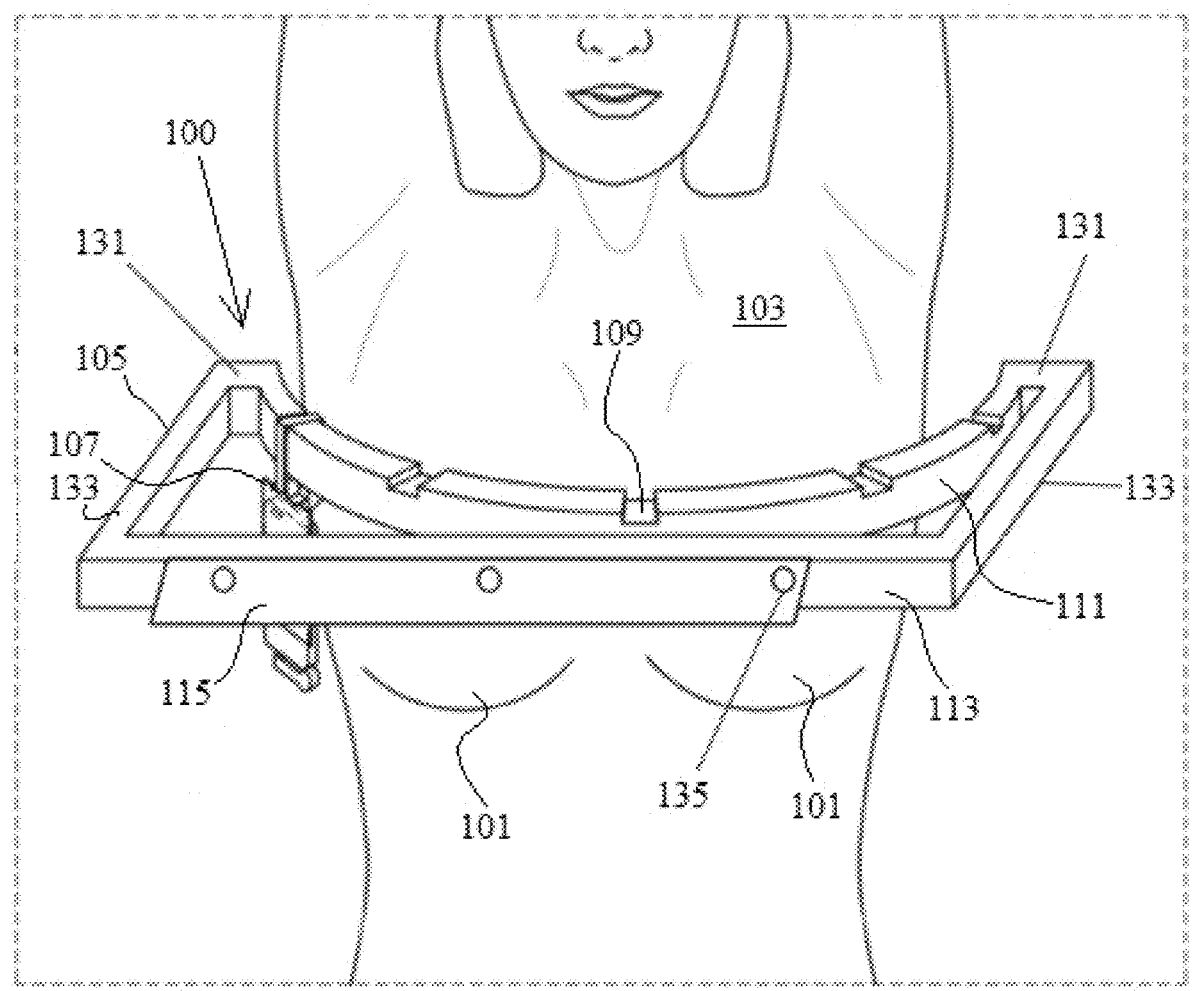
FIG. 1 is a perspective view of an embodiment of a system in accordance with this disclosure, showing a user screening herself.

Reference will now be made to the drawings wherein like reference numerals identify similar structural features or aspects of the subject disclosure. For purposes of explanation and illustration, and not limitation, an illustrative view of an embodiment of a system in accordance with the disclosure is shown in FIG. 1 and is designated generally by reference character 100. Other embodiments and/or aspects of this disclosure are shown in FIGS. 2-6.

Figure 2:
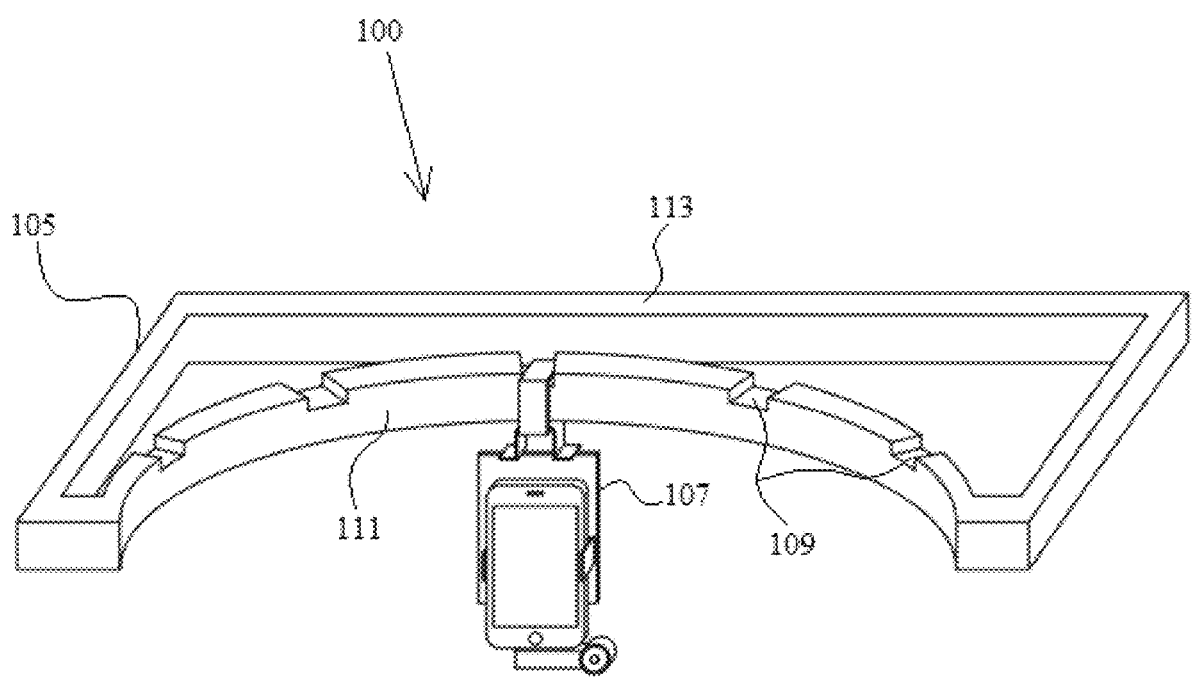
FIG. 2 is a perspective view of the system of FIG. 1.

Referring to FIGS. 1 and 2, a system 100 for imaging a portion 101 of a body 103 (e.g., a human body) can include a mount 105 configured to hold an imaging device carrier 107. The mount 105 can include a plurality of discreet positions (e.g., notches 109 as described below) configured to hold the imaging device carrier 107, for example.

In certain embodiments, the mount 100 can include a holder portion 111 configured to at least partially surround a portion 101 of a human body 103 and/or to provide a plurality of imaging angles of a human body 103. In certain embodiments, the holder portion 111 can have an arcuate shape, for example. In certain embodiments, the arcuate shape can be a half ellipse, e.g., as shown. Any other suitable shape is contemplated herein.

The holder portion 111 can include a plurality of notches 109 defined therein configured to receive the imaging device carrier 107. The plurality of notches 109 can include three or more notches 109, e.g., five notches 109 as shown. In certain embodiments, each notch 109 can be equally spaced apart from each other along the holder portion 111. Any other suitable number of notches 109 and/or spacing (e.g., unequal spacing) are contemplated herein. The notches 109 can include any suitable shape (e.g., complimentary to the imaging device carrier 107 or otherwise shaped to allow insertion of a portion of the imaging device carrier 107).

The mount 105 can include a wall mount portion 113 configured attach to a wall bracket or portion thereof (e.g., first portion 115), and/or to mount directly to a wall (not shown). The wall mount portion 113 can be straight and/or flat, e.g., as shown.

The system 100 can include a first portion 115 of a wall bracket configured to be attached to (e.g., and/or attached to) the wall mount portion 113 of the mount 100. The system 100 can include a second portion (not shown) of a wall bracket configured to attach to a wall (e.g., via one or more fasteners) such that the mount 105 can be configured to removably and/or moveably connect to the wall to position the mount 105 in the same position during imaging. In certain embodiments, the wall bracket can be a z clip, e.g., such that first portion 115 is a first portion of a z clip and the second portion (not shown) is a complimentary wall mounted portion of the z clip). Any suitable mounting to a wall or any other object, and any suitable mounting bracket assembly for providing consistent images is contemplated herein.

In certain embodiments, the system 100 can include the imaging device carrier 107. The imaging device carrier 107 can be configured to be removably and/or moveably held by the mount 105. The imaging device carrier 107 and/or the mount 105 can include a level (not shown) disposed thereon to ensure that the imaging device carrier 107 is level at each use. The imaging device carrier 107 can be configured to hang from the mount 105, e.g., the holder portion 111 as shown.

In certain embodiment, the imaging device carrier 107 can include a clamp 117 (e.g., having a spring loaded moveable portion and a fixed portion) configured to hold an imaging device 119. The imaging device carrier 107 can include any other suitable structure configured to hold any suitable imaging device 119.

Figure 3:
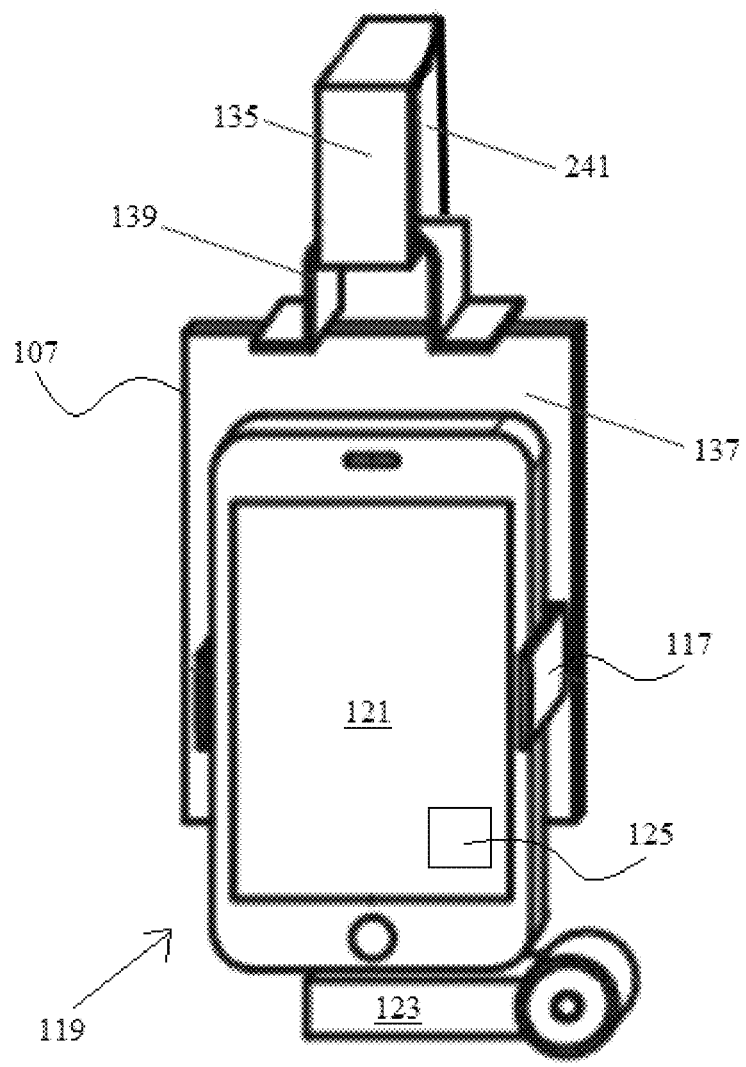
FIG. 3 is a perspective view of an embodiment of an imaging device carrier, shown holding an imaging device.

Referring additionally to FIG. 3, in certain embodiments, the imaging device can include portable electronic device 121 (e.g., a smartphone or tablet) and a thermal imaging device 123 connected to the portable electronic device 121.

Figure 4:
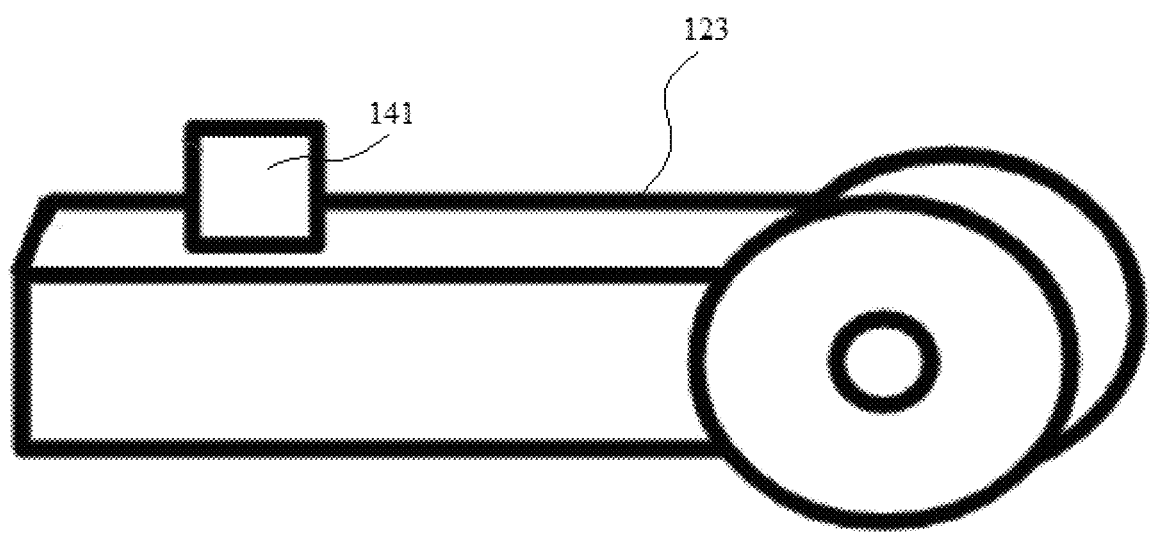
FIG. 4 is a perspective view of an embodiment of a thermal camera plugin, e.g., for a smart device to operate as a thermal imaging device.

In certain embodiments, e.g., as shown in FIG. 2, the system 100 can include an imaging module 125. The imaging module 125 can include any suitable hardware and/or software modules configured to perform any suitable function(s) and/or method(s) disclosed herein. In certain embodiments, the imaging module 125 can be a software application (e.g., an "app") for a smartphone. The imaging module 125 can include any suitable graphical user interface (GUI), e.g., as shown in FIG. 4, for operating the imaging device 119 and/or for calibrating the imaging device 119, and/or presenting data and/or one or more images to a user.

In certain embodiments, the imaging module 125 can be configured to receive one or more thermal images of the body portion 101 from the imaging device 119 and to allow a user to screen for a medical condition (e.g., breast cancer) of the body portion 101 (e.g., breasts as shown). In certain embodiments, the body portion 101 can be breasts, and the medical condition can be breast cancer. Any other suitable medical condition determinable by suitable imaging at any suitable portion of the light spectrum (e.g., infrared for thermal) is contemplated herein.

Figure 5:
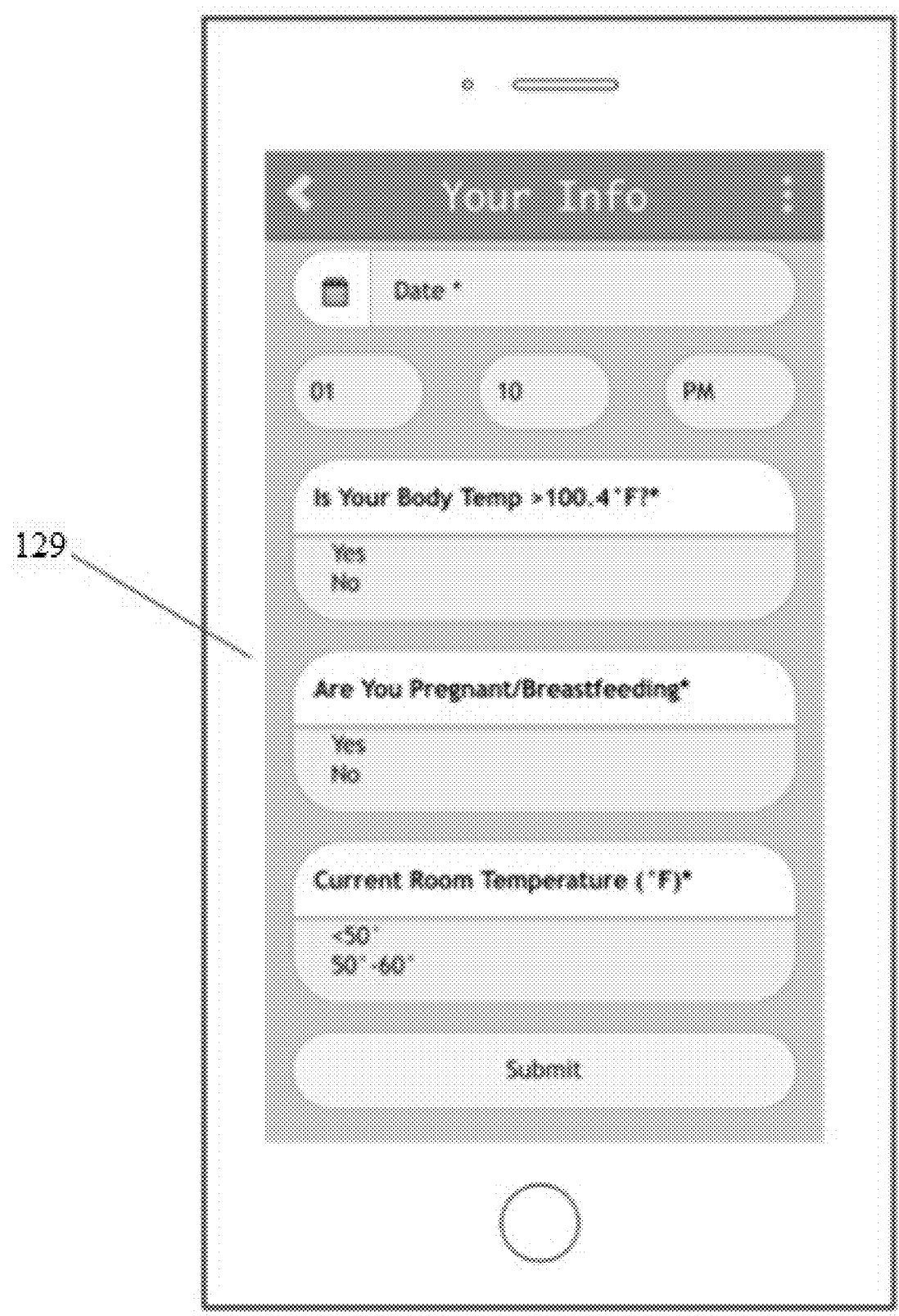
FIG. 5 is a schematic view of a graphical user interface of an imaging and/or analysis module, e.g., for a smart device.

The imaging module 125 can be configured to present one or more thermal images of the body portion to a display (e.g., of the portable electronic device 121) for a user to review (e.g., showing a side by side of the same thermal image with different filtering to view areas of certain heat signatures as shown in FIG. 5). In certain embodiments, the imaging module 125 can be configured to allow the user to monitor changes of a plurality of thermal images of the body portion 101 over time (e.g., by presenting a plurality of images from different dates overlaid sequentially or presented relative to each other in any other suitable manner). In certain embodiments, the imaging module 125 can be configured to analyze the one or more thermal images for a medical condition (e.g., by comparing thermal images from different dates together to determine if a hot region has become larger, e.g., by a threshold amount). The imaging module 125 can be configured to present results of analysis to a display of a device (e.g., of device 121). Any suitable combination of the above functions is contemplated herein.

In certain embodiments, the imaging module 125 can ask screening questions for efficacy of the thermography method. For example, the imaging module 125 can provide a GUI 129 as shown in FIG. 4. The GUI 129 can include any suitable questions relating to any suitable factors affecting accuracy of the thermal images (e.g., a fever, pregnancy/breastfeeding, extreme room temperatures, etc.). In certain embodiments, the imaging module 125 can provide information with images letting user know that images were taken under less than ideal circumstances and/or the imaging module 125 can be configured to filter and/or account for the variables.

The imaging module 125 can include any other suitable module(s) having any other suitable function(s). The imaging module 125 can be configured to perform any suitable method(s) and/or function(s) disclosed herein.

The system 100 can include any other suitable components. Certain embodiments of the system 100 can be packaged as a kit having the physical components of the mount 105, the carrier 107, any suitable wall bracket and/or portions thereof if included, and a thermal imaging device 123 (e.g., an attachable device to a smartphone). The kit can include instructions to download and/or install the imaging module 125 on a portable electronic device.

Embodiments can be or include an apparatus and a method for detecting breast cancer using thermography. FIG. 1 shows a user taking a series of thermal images of her breasts. A woman can be recommended to screen herself once per month using a mount 105 as shown in FIGS. 1 and 2. This mount 105 can be used in order to take images of breasts at one or more consistent angles, e.g., once each month, so as to load onto an imaging module 125 to screen herself for breast cancer. This mount 105 can include a holder portion 111 that can be in the shape of a half ellipse, for example, with a major axis slightly larger than the width of an average sized human. The mount 105 can include outward ends 131 of the half ellipse that can extend away (e.g., horizontally) from the half ellipse slightly. The mount 105 can include extending ends 133 that can extend behind the half ellipse and can be connected by the wall mount portion 113. The mount 105 can be attached to the wall from the wall mount portion 113 by a first bracket portion 115, e.g., a z-clip which can be attached to the mount 105 and connected to an adjoining z-clip (not shown) which is attached to the wall. The first bracket portion 115 and/or the second bracket portion can have a plurality of holes 135 that can be used for attachment to both the wall and mount 105 by screws, for example. The mount can have five notches 109 which can allow for a imaging device carrier 107 to slide around the mount 105 and stop at consistent places. These notches 109 can be approximately equally spaced around the half ellipse. Certain embodiments can also include a retractable string (not shown) or any other suitable instrument that comes out of the center of the mount 105, to ensure that the user is the same distance from the mount 105 during each screening.

Embodiments can include an imaging device carrier 107, e.g., as shown in FIGS. 2 and 3, which can be used to slide across the half ellipse and hold the portable electronic device 121 and thermal imaging device 123. This imaging device carrier 107 can stop in the notches 109 to take consistent images in the same locations and angles. The carrier can be made up of a slider 135, a support plate 137, a hinge or connector 139, and an adjustable clamp 117. The slider 135 can include four rectangular pieces 241. This slider 135 can fit snugly in the notches 109 on the mount 105. The slider 135 can be attached to the support plate 137 by the hinge or connector 139. This support plate 137 can hold an adjustable clamp 117 which can attach to an imaging device 119. A thermal imaging device 123 can attach to a portable electronic device 121 (e.g., a mobile device 121) to form the imaging device 119, for example.

The infrared thermal imaging device 123 can be compatible with most smart mobile devices and can be used for the imaging of breasts, for example, or any other suitable body portion. As shown in FIG. 4, the thermal imaging device 123 can include a portable device adapter 141. This portable device adapter 141 can include Android, Google, and Apple variations, for example. The images taken from this thermal imaging device 123 can be loaded onto the imaging module 125.

Figure 6:
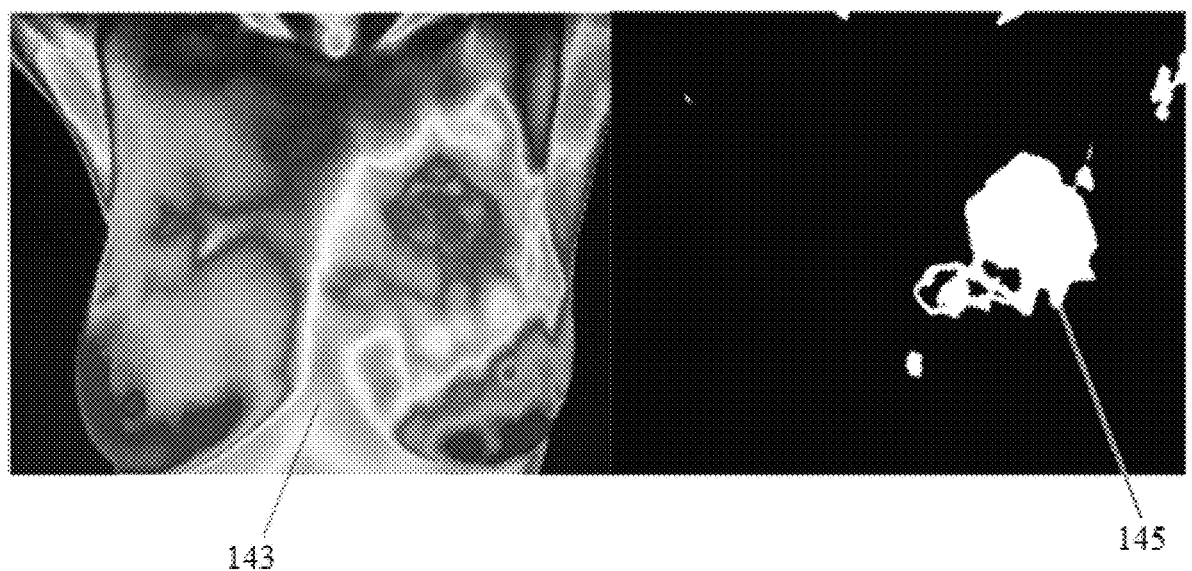
FIG. 6 is an embodiment of a thermal image of breasts next to an image of the breasts with recognized hotspots determined by the imaging and/or analysis module.

Embodiments of an imaging module 125, e.g., a software application, is shown in FIGS. 5 and 6, and can prompt a user to fill out a programmed questionnaire to learn information such as age, family history, pregnancy, etc. The imaging module 125 can prompt and guide the user to load thermal images 143 each month onto the mobile imaging module 125. The imaging module 125 can learn the thermal patterns of the user's breast throughout the months by a suitable learning and/or comparison algorithm (e.g., pixel growth). The imaging module 125 can analyze temperature differences between the two breasts each month, temperature changes throughout the months in the breasts, and a change of vascular patterns, for example. Embodiments can locate "hot spots" 145 which can be portions of the thermal breast image 143 that are greater than one degree celsius warmer than the rest of the breast.

The imaging module 125 can recommend (e.g., via an in-app prompt to the GUI, via a text message, or via any other suitable notification system) that the user receives her annual mammograms, regardless of the state of her thermal images. If the user is demonstrating signs of cancer, the imaging module 125 can recommend that she scan herself once each week, to reduce the chance of a false positive result. If the woman is consistently demonstrating signs of breast cancer, the imaging module 125 can recommend that the user visit a physician for further screening. In certain embodiments, one iteration of imaging can allow for the user to outsource their images to a physician if desired.

In certain embodiments, the imaging module 125 may play back any three or more sequential images that were taken at, e.g., one month intervals. In certain embodiments, the imaging module 125 can overlay the images and show them in a looping fashion so that the woman can see the changing vascular patterns over the arbitrary time period. In certain embodiment, the imaging module 125 can scan the images and can point to a recognized hotspot 145 which can add to the looping fashion. In certain embodiments, the camera's auto-scale can be turned off so there is not a glaring change as the images are cycled through. In certain embodiments, the imaging module 125 can standardize each image based on the user's average body temperature, in order to make each image comparable each month.

In accordance with at least one aspect of this disclosure, a mount, e.g., 105 for imaging a body part can be configured to hold an imaging device carrier and can include a plurality of discreet positions configured to hold the imaging device carrier. Any suitable embodiment of a mount disclosed herein, e.g., as described above, is contemplated herein.

In accordance with at least one aspect of this disclosure, a non-transitory computer readable medium can include computer executable instructions configured to cause a computer to perform a method. The method can include receiving one or more thermal images of a body portion from an imaging device, analyzing the one or more thermal images for a medical condition of the body portion, and presenting the one or more thermal images and/or analysis and/or one or more derivative images based on the one or more thermal images to a user for evaluating and/or monitoring the body portion. Any other suitable method(s) and/or portion(s) thereof are contemplated herein.

Embodiments can be or include a mount that can be mounted to any suitable upright system or wall, for example. Embodiments can be configured to be in same relative position (e.g., on the wall) each time. For a wall application, embodiments can include a mounting bracket that can screw into the wall or otherwise attached to the wall, and the mount can then attach to the mounting bracket. Embodiments of a mount can define an aperture configured to define standing area to partly surround the user. Embodiments can be arcuate or semicircular but can also be any other suitable shape. Embodiments can be adjustable or fixed, for example. Embodiments can include notches, which can be symmetric or not, and can be evenly spaced, shaped, or sized, or not. Embodiments can include a hanging camera carrier; however, embodiments can be configured to allow the holder to be above the mount on any suitable mechanism. Embodiments of a carrier can include any suitable clamp and/or surfaces to ensure the imaging device is in same position each time (e.g., a height limit or an indicator line instead).

Embodiments of an imaging module can be configured to use thermal images. Embodiments of a thermal camera can create a spectrum of colors based on heat. The imaging module can use a base point on the on body to calibrate temperature of body so that all images can be consistent irrespective of body heat at the time of imaging. The imaging module can be configured to see hot spots and compare the hot spots from one image in a mount position to one or more subsequent images (e.g., at least two images from different times) in the same position. The imaging module can be configured to determine and notify of a sufficient change over time (e.g., an increase in pixel size of a hot spot in one or more axes). Any other suitable image analysis (e.g., neural networks AI for evaluating any suitable condition such as increased blood in veins around tumor) is contemplated herein.

Certain embodiments of an imaging module may not evaluate and may only isolate hotspots and provide a time lapse of images in one or more positions. Time lapse can be provided in either an overlay, in a .gif file, or an animation of all the images, for example. In certain embodiments, options provided by the imaging module after imaging can include looking at one breast or both, can choose color overlay or black and white isolated images.

Embodiments can be used as a non-invasive and at-home screening method for breast cancer detection using thermography. Embodiments can take thermographic images of a user's breasts, e.g., once a month or at any other suitable interval, at specific angles set by a removable wall mount, and can include an application and algorithm that analyzes these images by comparison of temperature and vascular patterns between the breasts over a period of several months, for example.

Embodiments allow evaluation of thermal properties of a user's breasts (or other suitable body part) over time. Embodiments can provide a structure that can ensure consistent angles of incidence when capturing thermal images. Embodiments provide an at-home, non-invasive, easy-to-use and easy-to-interpret device for self-breast examination using thermography which can be used as an additional screening tool to mammography (or potentially as a primary screening process). Embodiments can permit a user to review her breast cancer status without the aid of a physician or specialized professional. Embodiments can make up for the infrequency of administration of mammograms and allow a user to be in control of her own health care.

Certain embodiments can include an inexpensive infrared camera that can interfaces to a user's cellphone, a screening app on the user's cellphone, and a wall mount. The user can employ the infrared camera to periodically take thermal images of her breasts. These images can be transmitted to the user's cellphone. The wall mount can facilitate the creation of thermal images that are consistent in scale and orientation. The app color can correct these images and produce animations that track the evolution of vascular patterns and asymmetries in the user's breasts over time. The wall mount can allow the user to take thermal images of her breasts over a wide range of angles of incidence to increase the reliability of the screening system. The system can be used in addition to regular doctor examinations, for example.

Certain embodiments include a system that screens for breast cancer using infrared thermal imaging by means of an adjustable mount and an infrared camera add on to a mobile device. The device can be an at-home, painless, and non-invasive system for self-breast examination using thermography to be used as an additional or alternative screening tool to mammography.

The device can include an infrared camera with a thermal sensitivity of 70 mK, for example, such as the Seek Compact Pro (mfg. by the Seek Thermal Corp.). The camera can plug into a cell phone. The camera and cell phone can be supported by a carrier attached to a removable wall-mounted bracket. The carrier and bracket can permit the camera and phone to be stably and accurately placed at, e.g., five equally-spaced locations around the user's chest, where individual thermal photographs can be taken by the user or automatically by the phone at timed intervals.

In certain embodiments, the mount can be removable from the wall. When the carrier is in the center position (directly opposite the center of the user's chest), the user can be prompted to pull a retractable string to her chest wall (above the center of her breasts). This can ensure that the user is the correct distance from the stand and that this distance is consistent between uses. This system can allow the user to take infrared images of their breasts at consistent positions.

The user can be recommended to screen herself once each month using this device, and the device will load these thermal images onto a mobile application. The application can include an algorithm that will perform a variety of functions. The app can stitch together an animation of the images at each angle from each month, so that the time evolution of any hot spots can be observed. The app can also pinpoint hot spots and compare them from month-to-month to see noticeable and obvious changes. The images can be analyzed in three ways. Changes (asymmetries) can be monitored between the two breasts each month, and changes within each breast between the months, and changes in vascular patterns each month, for example. Any other suitable timeline is contemplated herein. If changes are observed to be clinically significant, the app can recommend that the user screen herself once a week rather than once a month to reduce the likelihood of a false positive. If these changes continue to be significant, the app can recommend that the user visits her doctor for further screening. The user can then be able, via the app, to securely forward these images to her doctor in a manner consistent with the requirements of HIPAA, for example.

As will be appreciated by those skilled in the art, aspects of the present disclosure may be embodied as a system, method or computer program product. Accordingly, aspects of this disclosure may take the form of an entirely hardware embodiment, an entirely software embodiment (including firmware, resident software, micro-code, etc.), or an embodiment combining software and hardware aspects, all possibilities of which can be referred to herein as a "circuit," "module," or "system." A "circuit," "module," or "system" can include one or more portions of one or more separate physical hardware and/or software components that can together perform the disclosed function of the "circuit," "module," or "system", or a "circuit," "module," or "system" can be a single self-contained unit (e.g., of hardware and/or software). Furthermore, aspects of this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of this disclosure may be written in any combination of one or more programming languages, including an object oriented programming language such as Python, Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of this disclosure may be described above with reference to flowchart illustrations and/or block diagrams of methods, apparatus (systems) and computer program products according to embodiments of this disclosure. It will be understood that each block of any flowchart illustrations and/or block diagrams, and combinations of blocks in any flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in any flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

The articles "a", "an", and "the" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

Any suitable combination(s) of any disclosed embodiments and/or any suitable portion(s) thereof are contemplated herein as appreciated by those having ordinary skill in the art in view of this disclosure.

The embodiments of the present disclosure, as described above and shown in the drawings, provide for improvement in the art to which they pertain. While the subject disclosure includes reference to certain embodiments, those skilled in the art will readily appreciate that changes and/or modifications may be made thereto without departing from the spirit and scope of the subject disclosure.

What is claimed is:

1. A system for imaging a portion of a body, comprising:
a mount configured to hold an imaging device carrier, wherein the mount comprises:
a plurality of discreet positions configured to hold the imaging device carrier;
a holder portion configured to at least partially surround a portion of a human body and/or to provide a plurality of imaging angles of a human body, wherein the holder portion includes three or more notches defined therein configured to receive the imaging device carrier, each notch equally spaced apart from each other along the holder portion; and
a wall mount portion configured attach to a wall bracket or portion thereof, and/or to mount directly to a wall.

2. The system of claim 1, wherein the holder portion has an arcuate shape.

3. The system of claim 2, wherein the arcuate shape is a half ellipse.

4. The system of claim 1, wherein the wall mount portion is straight and/or flat.

5. The system of claim 4, further comprising a first portion of a wall bracket configured to be attached to the wall mount portion of the mount and a second portion of a wall bracket configured to attach to a wall such that the mount is configured to removably and/or moveably connect to the wall to position the mount in the same position during imaging.

6. The system of claim 5, wherein the wall bracket is a z clip.

7. The system of claim 1, further comprising the imaging device carrier configured to be removably and/or moveably held by the mount.

8. The system of claim 7, wherein the imaging device carrier and/or the mount includes a level disposed thereon to ensure that the imaging device carrier is level at each use.

9. The system of claim 7, wherein the imaging device carrier is configured to hang from the mount.

10. The system of claim 9, wherein the imaging device carrier includes a clamp configured to hold an imaging device.

11. The system of claim 7, further comprising an imaging module configured to receive one or more thermal images of the body portion from the imaging device and to allow a user to screen for a medical condition of the body portion.

12. The system of claim 11, wherein the body portion is breasts, wherein the medical condition is breast cancer.

13. The system of claim 11, wherein the imaging module is configured to present one or more thermal images of the body portion to a display for a user to review, and/or to allow the user to monitor changes of a plurality of thermal images of the body portion over time, and/or to analyze the one or more thermal images for a medical condition.

14. A mount for imaging a body part configured to hold an imaging device carrier, comprising:
a plurality of discreet positions configured to hold the imaging device carrier;
a holder portion configured to at least partially surround a portion of a human body and/or to provide a plurality of imaging angles of the human body; and
a wall mount portion configured attach to a wall bracket or portion thereof, and/or to mount directly to a wall.

15. A system for imaging a portion of a body, comprising:
a mount configured to hold an imaging device carrier, wherein the mount includes a plurality of discreet positions configured to hold the imaging device carrier; and
the imaging device carrier configured to be removably and/or moveably held by the mount, wherein the imaging device carrier and/or the mount includes a level disposed thereon to ensure that the imaging device carrier is level at each use, wherein the imaging device carrier is configured to hang from the mount, and wherein the imaging device carrier includes a clamp configured to hold an imaging device.

\* \* \* \* \*